(12) United States Patent
Motoi

(10) Patent No.: US 7,110,826 B2
(45) Date of Patent: *Sep. 19, 2006

(54) COSMETIC USE ALTERNATING CURRENT WAVE FORMS AND COSMETIC DEVICE

(76) Inventor: Shingo Motoi, Shinjuku-ku, 4-Chōme, 3-15 Rayflat-Shinjuku, 1104, Tokyo, 160-0022 (JP)

( * ) Notice: Subject to any disclaimer, the term of this patent is extended or adjusted under 35 U.S.C. 154(b) by 548 days.

This patent is subject to a terminal disclaimer.

(21) Appl. No.: 10/410,639

(22) Filed: Apr. 9, 2003

(65) Prior Publication Data

US 2003/0191508 A1   Oct. 9, 2003

Related U.S. Application Data

(63) Continuation-in-part of application No. 09/515,444, filed on Feb. 29, 2000, now Pat. No. 6,584,359.

(30) Foreign Application Priority Data

Jan. 18, 2000   (JP)   ................................. 2000-8971

(51) Int. Cl.
*A61N 1/32* (2006.01)

(52) U.S. Cl. ............................. 607/76; 607/48; 607/50; 607/115

(58) Field of Classification Search .................. 607/50, 607/76, 48, 115

See application file for complete search history.

(56) References Cited

U.S. PATENT DOCUMENTS

| 5,433,735 | A  | * | 7/1995 | Zanakis et al. | ................ | 607/50 |
| 6,249,706 | B1 | * | 6/2001 | Sobota et al.  | ................ | 607/115 |
| 6,947,791 | B1 | * | 9/2005 | Zhang et al.   | ................ | 604/20 |

* cited by examiner

*Primary Examiner*—Scott M. Getzow
(74) *Attorney, Agent, or Firm*—Ohlandt, Greeley, Ruggiero & Perle, LLP; George W. Rauchfuss, Jr.

(57) ABSTRACT

A beauty device is provided that offers conditions that are appropriate for electrical stimulation that is designed to resolve wrinkling, sagging and such of skin conditions.

A pair of electrically conductive gloves and that include silver conductive material is worn on both hands that have been clad in insulated gloves. A combination of ultra-weak electrical currents that are comprised of a combination of multiple types of current wave forms made up of alternating current square-waves of differing patterns are provided from the electrical current control device and applied to the surface of the skin in areas such as the face through the electrically conductive gloves by having the gloves come into contact with the skin, thereby reducing the wrinkles, sagging and such of the skin.

24 Claims, 6 Drawing Sheets

COSMETIC USE ALTERNATING CURRENT WAVE FORMS AND COSMETIC DEVICE

RELATED APPLICATION

This application is a continuation-in-part of allowed application Ser. No. 09/515,444, filed Feb. 29, 2000 now U.S. Pat. No. 6,584,359.

FIELD OF THE INVENTION

This invention relates to a technology that applies very weak electrical stimulation to skin for the objective of the health, beauty and such of skin, and in particular, it relates to a cosmetic device that has specific alternating current wave forms that have a cosmetic effect and that conduct very weak electrical current that have such specific alternating current wave forms.

BACKGROUND OF THE INVENTION

An electrical current that is called biological electrical current flows through live cells, tissues, bodies and such. Biological electrical current is involved in many instances of the human biological activities such as cardiac and pulmonary functions, gastrointestinal peristaltic movements, and the bending of the limbs. Biological electrical current occurs on account of the electric potential differences inside and outside the cells that constitute all the body tissues.

In human bodies, biological electrical currents are constantly flowing while delicate electrical balancing is constantly taking place from the dermal pars profunda to the surface of the skin as smooth metabolism is maintained and the functions of the skin are preserved. Biological electrical currents are influenced by factors such changes in the body's condition and aging, but there are situations when it is weakened and when that happens, it is not possible to preserve the delicate electrical balance within the body. If such a state of imbalance continues, health problems and beauty problems result as the functions within the body deteriorate at a slow pace, the working of the cells weaken, aging of the muscles occurs, and such.

As a method for treating health problem, in the field of oriental medicine there is electrical treatment in which electrical stimulation is applied by conducting electrical current to one of the numerous acupuncture points along the meridians of the human body. In electrical therapy, the voltage used at the needle tip is 7 to 10 volts, which is considerably higher than that of biological electrical current. In conducting electricity, depth needles that are the same as those used in acupuncture therapy are used as probes to stimulate the acupuncture points.

However, in the above-described electrical therapy, because narrow needles are used as the probes, much time is required with a depth needle to probe in an acupuncture point. Also, because the area that is in actual contact with the needle point is very small, the possibility that the position at which stimulation is applied may be off the mark is high. Because of this, unless there is one who is experienced and knows enough about the acupuncture points and meridians, it is difficult to appropriately conduct such electric therapy.

Also, when examined in detail, it is seen that sufficient electrical stimulation cannot be applied to an acupuncture point. Furthermore, when a depth needle is inserted, unless it is inserted by someone like an experienced acupuncturist, there are cases where there is stabbing sensation pain.

To resolve these problematic points, a method entailing a device for the conduction of electricity that is comprised of a grounder connected to a circuit wherein the voltage can be changed and a glove that is connected to the above-described circuit for passing electricity and which has woven into it copper wiring that is in a thread-like form, with which the grounder is grasped with one hand and the other hand that is in an insulated state is clad in the glove with a finger of the gloved hand pressing against an acupuncture point has been laid open in Japanese Utility Model Sho. 53 (1978)-160289.

With this laid open method, an area of contact that is wider than that which is contact with a narrow depth needle is achieved, and it is possible to cover an acupuncture area even if the center of the acupuncture point might be missed by a slight degree. Even with electricity that is conducted with pressure, it is possible to achieve a broad area to which electricity is conducted, and there is not the concern that had existed about stabbing pain. Furthermore, with five fingers, it is possible to press against the acupuncture points of five locations at once, thus making it possible to apply stimulation by conducting electricity to a plural number of locations at once.

However, the above-described method is one with which a direct current applied to the acupuncture points is of a higher voltage than that of biological electrical current and which completely differs from the stimulation when electricity is conducted at biological electrical current levels.

Also, from a cosmetic perspective, there are a number of methods with for the stimulation of the skin of the face and such by conducting electricity that are similar in composition to the above-described electrical treatment device but the high voltage of these lends them to being given broad berth as products. From this perspective, there are cosmetic devices that are out on the market that are characterized by stimulation by conducting by means of very weak electrical currents at a low voltage, but of these there are ones which are thought to be merely ones in which the strength of the electrical current has been lowered, and there are also cases in which it is not possible to confirm their cosmetic efficacy.

Now, this inventor, keeping in mind such prevailing circumstances, by researching in earnest into the interdependence of the electrical current wave forms and the cosmetic effects and such, has come up with the appropriate conditions that relate to conducting electricity; and this inventor considered that it was necessary to develop a cosmetic device with which it would be possible to achieve cosmetic effects when used.

SUMMARY OF THE INVENTION

The objective of this invention is to make appropriate, from the perspective of cosmetic effects, the voltage of the stimulation electrical current, electrical current wave form and such in cosmetic technology wherein the cosmetic effects are obtained by means of electrical stimulation.

The skin treatment in which the cosmetic device in accordance with this invention is used, is performed by putting on both hands electrically conductive gloves with which good electrical conductivity is obtained by means of including electrically conductive material such as silver. The electrically conductive gloves are used by connecting them by means of a connection cord to an electrical stimulation control device that outputs alternating current wave form electrical currents that yield cosmetic effect. Furthermore, when putting on the electrically conductive gloves, although the voltage is low, these gloves can be put onto bare hands without damage but what is more desirable is to put on the gloves with both hands placed in an insulated state by taking action such as putting on insulated gloves. By putting the electrically conductive gloves on to hands that have been insulated, it is possible to assure more effective electrical stimulation effects on the locations where the stimulation is conducted from the electrically conductive gloves.

The minute electrical current of the alternating current with which it is possible to obtain cosmetic effects on the wrinkles, sagging and such of skin is made possible by means of conducting electrical stimulation that is supplied from an electric current stimulation device to the above-described electrically conductive gloves. Such alternating currents should be composed of a plural number of alternating currents of square-waves that are serially combined alternating current square-waves of differing patterns.

For the stimulation that results from passing electricity, this invention does not pass electrical current of wave forms that can essentially be considered to be of a single wave form but rather, as described above, combines alternating current square-wave of differing patterns, and thereby improves the cosmetic effects. By means of this, the skin on the receptor side of the electrical stimulation does not become habituated to the same series of electrical stimulation and the skin can sensitively respond to the electrical stimulation, and thus the electrical stimulation is useful in providing an improving cosmetic effect on the skin.

As a result of performing experiments in which various alternating current square-wave were combined repetitively, it was determined that it is possible to obtain dramatic cosmetic effects such that the effects are visually ascertainable for specific alternating current wave forms.

Thus, from the experiments of this inventor it was learned that a plural number of varieties of alternating current wave forms from the repetitive combination of differing alternating current square-waves patterns, types of wave forms, and the further repetitive combination of the alternating current wave form combinations is effective in cosmetic effect improvements such as on the wrinkles, sagging and such of the skin. For such cosmetic use alternating current wave forms, it was learned that the ones that possess the specific wave forms described below are even more effective.

For example, the alternating current wave forms are such that when the positive side electric potential level and the negative side electric potential level are indicated with the reference electric potential as the mid-point, the alternating current wave forms described above should be formed by the repetitive combination of one of the two electric potential levels and the indication of the other level the electric potential levels indicated once in an alternating square-wave pattern as a single pattern for the time interval of the 1st reference time as a single pattern, and the repetition of the afore-described single pattern thrice as the triple repetitive pattern, and the indication of the afore-described reference electric potential for twice the time of the 1st reference time as the pause, in the sequence of the afore-described triple repetitive pattern, the afore-described pause, the afore-described triple repetitive pattern, the afore-described pause, the afore-described single pattern, the afore-described pause, the afore-described single repetitive pattern, the afore-described pause, the afore-described single pattern, the afore-described pause, the afore-described single pattern and the afore-described pause.

As another way there are repetitive combinations of alternating current square-waves of the indication of one of the two electric potential levels indicated for the time of the 2nd reference time and the indication of the electric potential level of other for ½ of the time of the 2nd reference time as the 1st repetitive pattern and the alternating current square-waves of the indication of one of the afore-described electric potential levels for ½ of the time of the time of the afore-described 2nd reference time and the indication of the afore-described reference electric potential for ½ of the time of the time of the afore-described 2nd reference time and the indication of the other of the afore-described electric potential levels for ½ of the time of the afore-described reference time as an alternating current square-wave and the afore-described reference electric potential for ½ of the time of the time of the afore-described 2nd reference time as the pause, in the sequence of the afore-described 1st repetitive pattern, the afore-described pause, the afore-described 2nd repetitive pattern, the afore-described pause, the afore-described 2nd repetitive pattern, the afore-described pause, the afore-described 2nd pattern and the afore-described pause.

Or another way would be repetitive patterns of alternating current square-wave of the indication of one of the levels of the electric potential levels for the time of the 3rd reference time and the indication of the other level of afore-described electric potential levels for the time of the afore-described 3rd reference time and the indication of the other level of the afore-described electric potential levels for the time of the afore-described 3rd reference time and the indication of the other level of the afore-described the electric potential levels for the time of the afore-described 3rd reference time and the indication reference electric potential for twice the time of the afore-described 3rd reference time and the indication of the level of the afore-described one of the electric potential levels for ¼ of the time of the afore-described 3rd reference time and indication of the afore-described reference electric potential for ½ of the time of the afore-described 3rd reference time and indication of the one of the levels of the afore-described electric potential levels for ¼ of the time of the afore-described 3rd reference time and the indication of the levels of the afore-described reference electric potential for the time of the 3rd reference time and the indication of the other level of the afore-described the electric potential levels for ¼ of the time of the afore-described 3rd reference time and the indication of the reference electric potential for ½ of the time of the afore-described 3rd reference time and the indication of the other level of the afore-described electric potential levels for ¼ of the time of afore-described 3rd reference time and indication of the afore-described reference electric potential for the time of the afore-described 3rd reference time as the 3rd repetitive pattern of the alternating current square-wave, and the indication of the afore-described reference electric potential for the time of the afore-described 3rd reference time and the indication of the afore-described one of the levels of the electric potential levels for ¼ of the time of the afore-described reference time and the indication of the reference electric potential for ½ of the time of the afore-described 3rd reference time and the indication of the afore-described other level of the electric potential levels for ¼ of the time of the afore-described 3rd reference time as the repetitive pattern in one direction, and the indication of the reference electric potential for the time of the afore-described 3rd reference time and the indication of the afore-described other level of electric potential levels for ¼ of the time of the afore-described 3rd reference time and the indication of the reference electric potential for ½ of the time of the afore-described 3rd reference time and the indication of the afore-described other level of electric potential levels for ¼ of the time of the afore-described 3rd reference time as the repetitive pattern in the other direction and indication of the afore-described reference time for the time of the afore-described reference time as the pause, in the sequence of the afore-described 3rd repetitive pattern, the afore-described 3rd repetitive pattern, the afore-described repetitive pattern in one direction, the afore-described repetitive pattern in the other direction, the afore-described pause, the afore-described repetitive pattern in one direction, the afore-described repetitive pattern in the other direction, the afore-described pause, the afore-described repetitive pattern in one direction, the afore-described repetitive pattern in the other direction, the afore-described pause, the afore-described repetitive pattern in one direction.

Furthermore, when the wave form composed of the repetition of each of the above-described 3 specific wave form types used by further repeating the combination, from a cosmetic effect perspective, the results were superior to those obtained when each of the specific wave forms was used singularly. Regarding the combination these 3 specific wave form types, it was confirmed that effective cosmetic results can be obtained by setting the 2nd reference time to be quadruple the time of the afore-described 1st reference time and the afore-described 3rd reference time to be equal to the time of the afore-described 1st reference time.

Such a composition of the cosmetic use alternating current wave forms of this invention is such that it as similar as possible to the biological electrical current that occurs in live human bodies, and the electrical current should be a very weak one so that the operator will not be exposed to any danger as well as for the safety of the skin. For example, the voltage should be from about ±0.3 to about ±3.9 V and the electrical current stimulation should be applied under electrical conductivity conditions of 500 µA or less. While the device of this invention can provide a voltage of from about ±0.3 to about ±3.9 V the device is provided with an appropriate voltage selection switch so as to provide a selected range of voltage for sensitive skin areas and a higher selected range of voltage for a less sensitive skin areas. As a further example, with conductivity gloves that contain as a conducting material, such as for example silver as conductive material, for areas wherein the skin is sensitive, such as the face, the switch should provide a voltage of from about ±0.3 to about ±1.2 V, and a voltage within the range of from about ±0.9 to about ±3.9 V for areas where the surface skin is relatively thick, such as the body, and the electrical current stimulation should be applied under electrical conductivity conditions of 500 µA or less. Preferably, the gloves have a conducting material such that the electrical resistance of the electrical conducting gloves is 1 kΩ or less. In a preferred embodiment of the invention the device of the invention is adapted to repeatedly output the selected electrical voltage in a cycle time of about 12.8 seconds.

The lower limits of ±0.3 V and ±0.9 V or greater were established because significant difference in cosmetic effect could not be observed at lower levels. Also, the upper limits of ±1.2 V and ±3.9 V or less were established because these are the values at which a user can use the invention without sensing strong electrical stimulation and with ample safety.

The composition of the cosmetic device that is in accordance with this invention is such that it can be used for daily skin care by the simple use of electrical stimulation that is based on the cosmetic use alternating current wave forms, the composition of which is described above. For example, both hands are well insulated by wearing insulated gloves and placed in electrically conductive gloves that have good conductivity because they contain silver or such as conductivity material. These electrically conductive gloves are electrically connected by means of a connection cord to an electrical current stimulation device that outputs very weak electrical currents in alternating current wave forms that have the cosmetic effect that has been explained in the above description.

When the switch for the electrical current control device is turned ON, the required electrical current is output to the side of the electrically conductive gloves, and in this state, the electrically conductive gloves are brought into contact with the skin of the face, scalp or such; by this, the electrical current described above passes to the skin, and treatment is applied as the electricity is conducted, with the objective of improving the wrinkling, sagging and such of the skin.

BRIEF DESCRIPTION OF THE DRAWINGS

The invention will be described in reference to the accompanying drawings in which.

DETAILED DESCRIPTION OF INVENTION AND PREFERRED EMBODIMENTS

Figure 1:
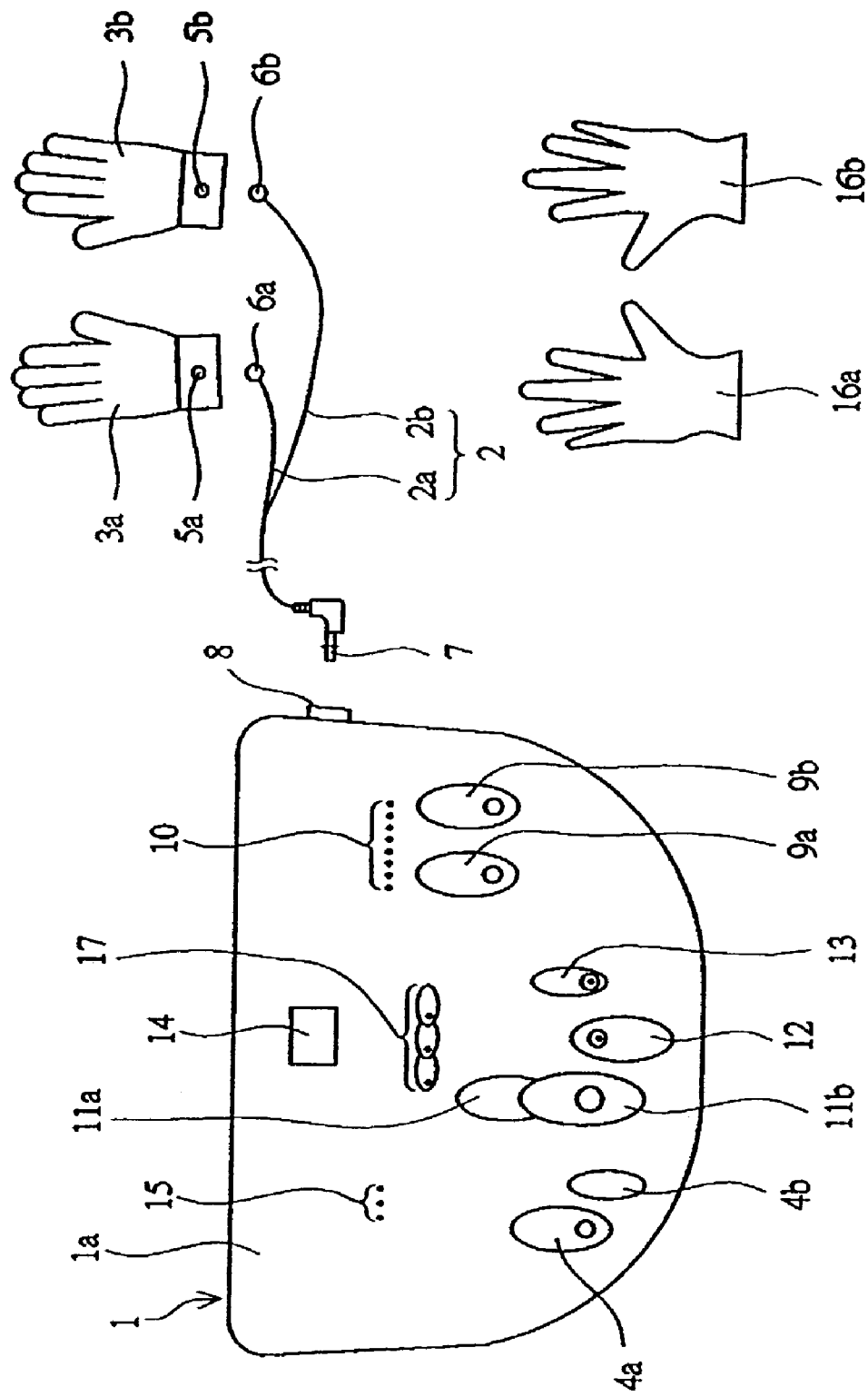
FIG. 1 is an explanatory diagram that depicts the composition of the cosmetic device in accordance with this invention.
Figure 2:
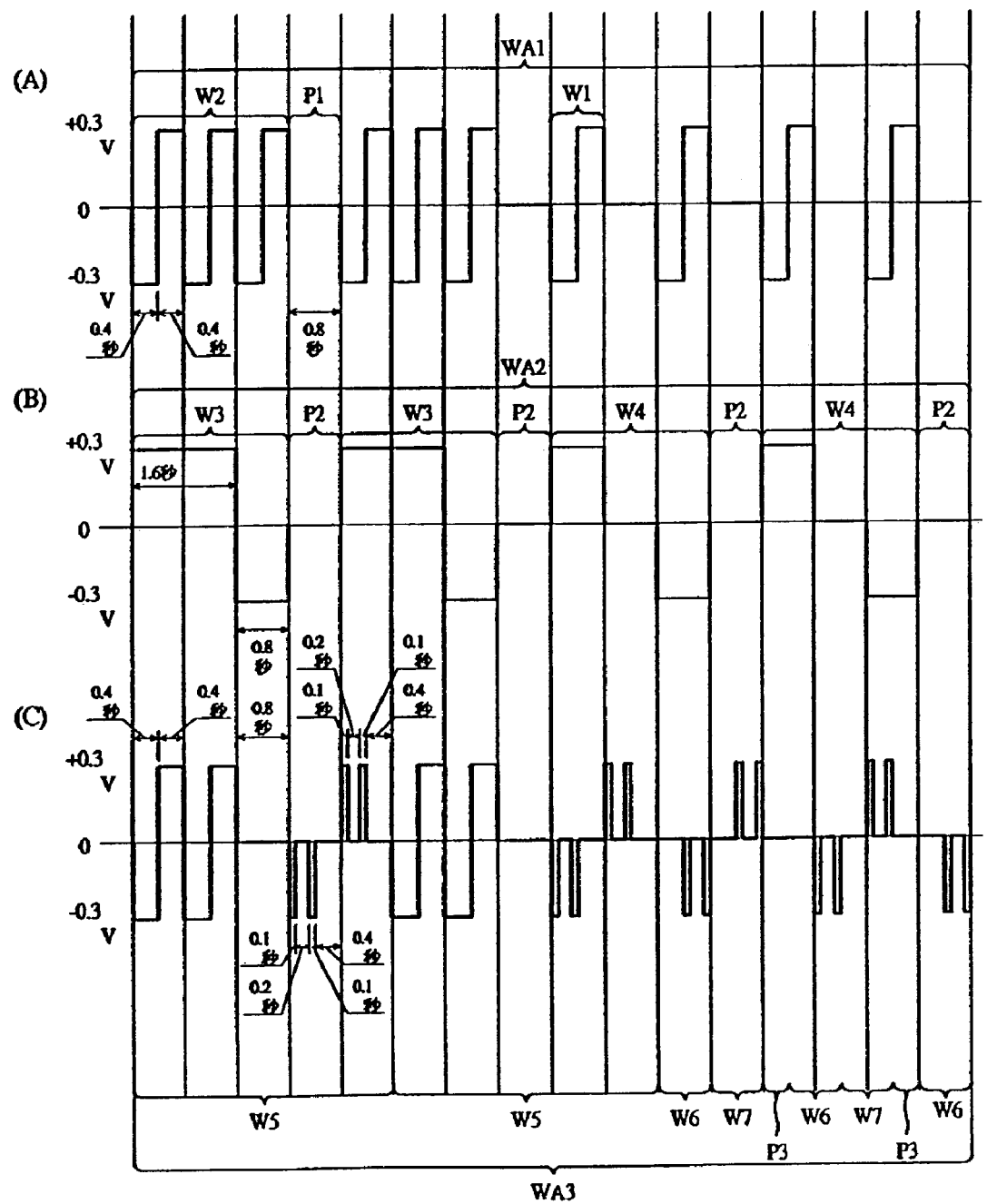
FIGS. 2(A), (B) and (C) are each diagrams that depict one example of one cycle of the cosmetic use alternating current wave form in accordance with this invention.
Figure 3:
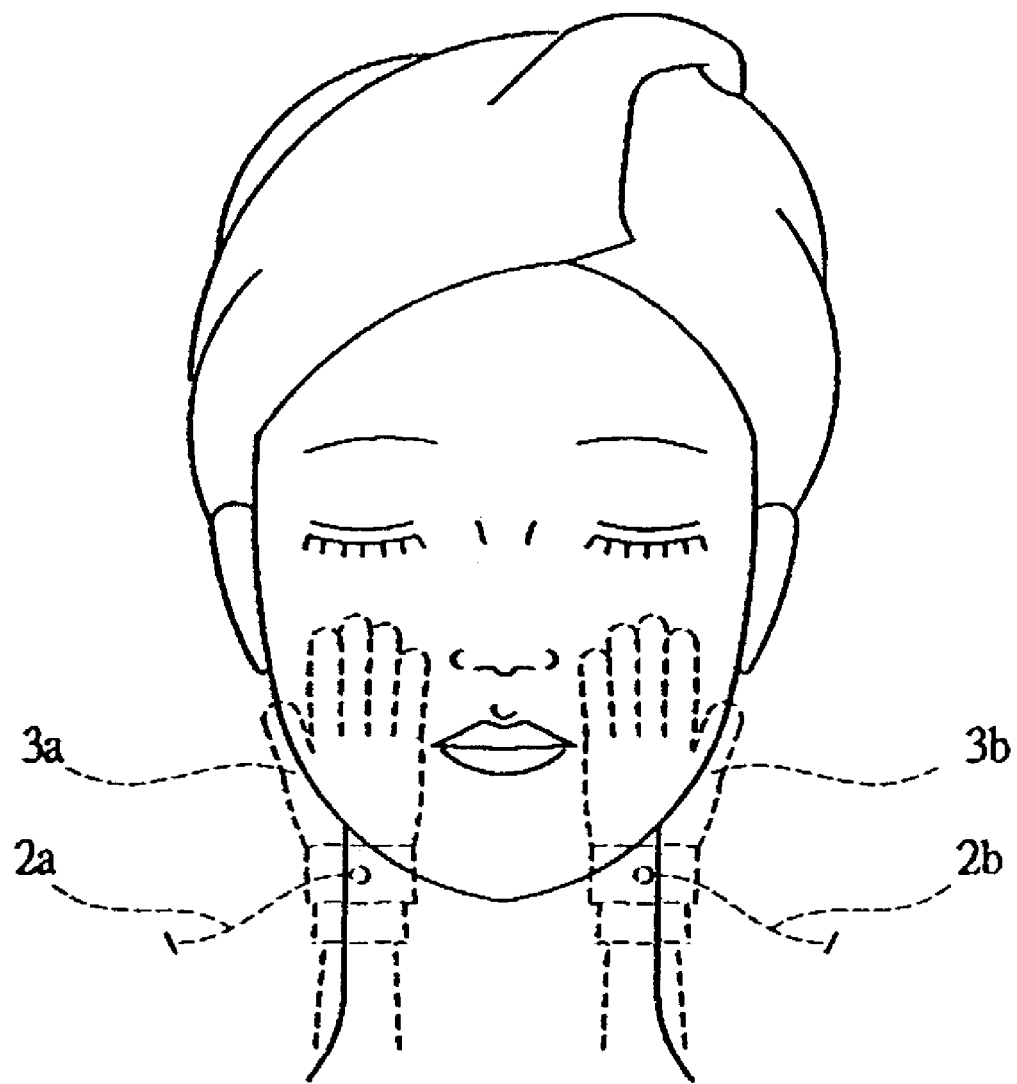
FIG. 3 is an explanatory diagram that depicts what happens when a facial treatment is given using the cosmetic use device in accordance with this invention.

The cosmetic use device is composed of an electrical current control device 1, a connection cord 2 and a pair of electrically conductive gloves 3a and 3b as shown in FIG. 1. Within the electrical current control device 1, is built-in an electrical current controller circuit that is not depicted in the figures; for example, it is possible to control the output voltage so as to repetitively combine the alternating current wave forms of the differing patterns in order to produce a plural number of alternating current square-waves, that are then subjected to further repetitive combining to output very weak electrical current in the form of the cosmetic use alternating current wave forms that are depicted in FIG. 2.

The operation panel 1a is established for the electrical current control device 1, and is depicted in FIG. 1. On this operational panel 1a have been established a touch type main switch 4a for turning the device ON and a main switch 4b for turning it OFF. By engaging the main switch 4a for turning the device ON, the device is rendered into a state in which it is possible to output very weak electrical current in cosmetic use alternating wave form to the electrical current control device 1. In this state, the electrically conductive gloves 3a and 3b are connected to the electrical current control device 1 by means of the connection cord 2

The electrically conductive gloves 3a and 3b are both made of an acrylic fiber or such that contains silver as a conductivity material. By means of including silver as a conductivity material, it is possible to impart good conductivity to the gloves. The quantity of silver that is contained should be such that the electrical resistance of the electrically conductive gloves is 1 kΩ or less. Comparing the quantity of conductivity material required when copper is used as a conductivity material, it is possible to limit the quantity of silver used.

By means of using silver as described above, when compared to using a conductive material that has a lower conductivity, such as copper, it is possible to reduce the voltage load of the alternating current that is conducted to the electrically conductive glove 3a, and it is possible to keep low the over all electric potential used to achieve stimulation by conducting electricity.

With a cosmetic use device, there is ample reason to consider that it will be often be used in the home and that wet hands are likely to come in contact with it. Because of this, by keeping the voltage that is used as low as possible, it is possible to operate the device safely as a cosmetic use device and to make sure that the unlikely occurrence of strong electrical stimulation does not come true.

Also, by means of the use of silver as a conductive material, as compared to when carbon is used as a conductivity material, it is possible to willfully achieve a desirable silver/white color. Furthermore, when used as a cosmetic use device, by means of the anti-bacterial characteristics of the silver that is used as a conductivity material, it is possible to protect the electrically conductive gloves from bacterial growth on the perspiration, skin oils and such, and of various bacteria that are apt to adhere on the gloves because of the anti-bacterial properties of silver that is used. That is why it is possible to prevent problems such as irritation of the skin from occurring by dealing with the source of such problems at the very source, the growth of bacteria on the surface of the electrically conductive gloves 3a and 3b.

The above-described composition of the electrically conductive gloves 3a and 3b is designed with hooks 5a and 5b that serve the role of connecting the electrically conductive gloves 3a and 3b to the connecting cord 2. The connecting cord 2 has a pair of lead lines, 2a and 2b, for the electrically conductive gloves 3a and 3b. At one end of the lead line pair, 2a and 2b, there are snaps 6a and 6b with the lead lines to be connected to hooks 5a and 5b of the electrically conductive gloves 3a and 3b when the gloves are put on and taken off the hands at will. The other end of the lead lines 2a and 2b are both connected to a common jack 7 in mid course.

By means of connecting the jack 7 of the connection cord 2 to the output terminal 8 of the electrical current control device 1, the alternating currents of the plural number of varieties of alternating current wave forms that result from the repetitive combination of the alternating current squarewaves of differing patterns and the further repetitive combination thereof to form the cosmetic use alternating current wave forms that are depicted on FIG. 2 are supplied to the electrically conductive gloves 3a and 3b.

With the electrical current control device 1, it is possible to change the range of the voltage of the alternating currents that are generated. For example, it is possible to switch between two alternating current voltage systems, one from ±0.3 V to ±1.2 V and the other from ±0.9 V to ±3.9 V. Each system is furthermore capable of changing the voltage in a plural number of stages. In terms of these systems, the electrical stimulation that is applied should be selected according to what is appropriate for the area of skin to which it being applied. For areas wherein the skin is sensitive such as that of the face, the smaller of the above-described voltages systems should be used and for the body and such wherein the thickness of the surface skin tends to be relatively thick, the higher voltage (for example that which is of a scope that is approximately 3 times that of the lower voltage scope) system should be used. As depicted in FIG. 1, the composition is such that the switching can be accomplished with eight levels shown by lead lamps 10.

On the operational panel 1a of the electrical current control device 1, a volume up switch 9a with which the voltage is raised one level at a time, and a volume down switch 9b with which the voltage is lowered one level at time have been established. A light emitting diode (LED) level lamp 10 has been established to indicate what is the prevailing voltage setting that can show each of the levels to which the voltage can be switched. It is possible to know what is the prevailing voltage level from which light emitting diode is lit.

Also, when setting which voltage system is to be used, when it is to be set so that is appropriate for the body, a facial select switch 11a and a body select switch 11b have been established for the mode selection.

A timer start/end switch 12 and a timer set switch 13 have been established. With the timer set switch 13, for example, it is possible to set the duration time for one of three settings—10 minutes, 15 minutes or 20 minutes. After setting the duration using the timer switch 13, it is possible to engage the timer start/end switch 12. If the timer start/end switch 12 is engaged after it has been initially engaged, the timer will disengage in the mid course. The duration that has been selected appears on the timer indicator window 14, and the composition is such that it is possible to know how much time is left from the digital display.

The electrical current control device 1 in accordance with this invention is such that it is possible to operate the device by means of the rechargeable built-in battery as an electrical power source. By using an adapter for recharging with alternate currents in a manner such that one end is connected to the electrical current control device 1 and the other end is connected to a household use electrical power source plug outlet, the built-in battery is charged making it possible to operate the device. To serve a gauge for seeing how much electrical charge remains in the battery, a battery checker 15 has been established; the prevailing situation is indicated by means of color differentiated light emitting diodes.

The cosmetic use composition described above of the device in accordance with this invention is used in the following manner. First of all, as is depicted in FIG. 1, both hands are inserted into insulation gloves 16a and 16b that are made of insulating material such as a synthetic resin like polyethylene or vinyl chloride to achieve insulation for both hands. It is also possible to achieve insulation by the use of liners that are made of insulating material and place inside the electrically conductive gloves 3a and 3b. Achieving insulation of both hands may be done using an appropriate hithertofore known method.

As described above, both hands are clad in insulation gloves 16a and 16b and thereby achieving insulation of both hands, and then both hands are place in the electrically conductive gloves 3a and 3b. Although as in the aforedescribed, extremely weak output voltage does go through the electrically conductive gloves 3a and 3b but in order to assure ample electrical conductivity, it is a good idea to wet the electrically conductive gloves 3a and 3b with a liquid such as water that has good electricity conduction characteristics.

On the other hand, at the connection point of the output terminal 8 of the electrical current control device 1, the lead lines 2a and 2b of the connection cord 2 to which the jack 7 has been inserted are hooked up in advance to the hooks 5a and 5b of the electrically conductive gloves 3a and 3b in order to prepare the electrically conductive gloves 3a and 3b for conducting electricity.

Under such conditions, the main switch 4a for turning the device ON is engaged, and then the facial select switch 11a or the body select switch 11b is selected and engaged in accordance with the treatment that is about to be given. At the same time, as required, the setting level for the output voltage may be changed.

If the output voltage is to be changed, the volume up switch 9a or the volume down switch 9b is engaged. In the event that the main switch 4b for turning the device OFF has been engaged and the use of the cosmetic use device has been concluded, the device is designed in such a way that at the electrical current control device 1, the output voltage will automatically be set once more at the lowest possible setting, thus making it unnecessary to confirm the setting for the voltage when starting to use the device. The device is designed in such a manner that even if a high voltage setting is the last one used, that high voltage setting will not be generated when the device is used the next time.

Using the electrically conductive gloves 3a and 3b that have been set in the manner outlined in the above description, for example, in the case that a facial treatment is going to be administered, the facial treatment switch 11a is selected. After the selection is made, the palm side of the electrically conductive gloves 3a and 3b into which both hands have been inserted are placed on the surface of the face and while slowly moving the hands, the palm side of the gloves cover the entire face in a manner such that the palm side of the gloves are in contact with the surface of the face. By taking such actions, the very weak electrical current is conducted from the electrically conductive gloves 3a and 3b to the skin of the face.

The treatment of the entire face that has been outlined in the above description is that which has the effect of supplementing the activation of the skin, and at this stage, as it is depicted in FIG. 2(A), it is desirable to use the cosmetic use alternating current square wave WA1 of the repetitive combination of the differing alternating current square-waves patterns.

For this cosmetic use alternating current wave form WA1, when the level of the positive side electric potential and the level of the negative side electric potential are indicated with the reference electric potential as the mid-point, the alternating wave forms should be composed a single pattern W1 in which is one of the levels of the two electric potential levels and the other level of the two electric potential levels for the time of the 1st reference time in an alternating manner, and a triple repetitive current pattern W2 that consists of a triple repetition of the single pattern W1, and a pause P1 that is composed of the indication of the reference electric potential for twice the time of the afore-described 1st reference time in a repetitive combination sequence of the triple repetitive current pattern W2, the pause P1, the triple repetitive current pattern 2, the pause P1, the single pattern W1, the pause P1, the single pattern W1, the pause P1, the single pattern W1, the pause P1, the single pattern W1 and the pause P1.

In particular, in cases such as depicted in FIG. 2(A), when the above-described 1st reference time is set at 0.4 second, which is to say that for an interval of 0.4 second, one of the levels of the two electric potential levels and the other level of electric potential levels are indicated in an alternating manner once to form a single pattern W1, and a triple repetitive pattern W2 wherein the single pattern is repeated thrice, and a pause 1 wherein the reference electric potential is indicated for 0.8 seconds in the repetitive combination sequence of the triple repetitive current pattern W2, the pause 1, the triple repetitive current pattern W2, the pause 1, the single pattern W1, the pause P1, the single pattern W1, the pause P1, the single pattern W1, the pause P1, the single pattern W1 and the pause P1.

The cosmetic use alternating current wave form WA1 that is described above is a wave form in which the above-described series combination is repeated in cycles of 12.8 seconds. By means of the repetition of this cosmetic use alternating current wave form WA1, while the very weak electrical current is being conducted, the preparatory treatment for the surface of the face that is outlined in the above description should be conducted.

After the conclusion of the above outlined preparatory treatment, the lift-up treatment which raises the wrinkles and such on relatively broad areas of the facial surface is conducted. This broad area life-up treatment is conducted with the palm side of the electrically conductive gloves 3a and 3b in contact with the surface of the face; as an example, the entire area of the cheeks is raised and that pose is kept. Those portions where what are commonly referred to as crows' feet occur around the eyelids, and the eyebrow area and the areas around the jaw and the corners of the mouth where laugh lines are apt to occur are also raised in a similar manner using the palms of the hands and maintaining that pose for a while; in other words, the area in question is lifted up. For such lift-up treatments, according to the experiments that have been conducted by this inventor, the use of the alternating currents of the of the cosmetic use alternating wave form WA2 that is depicted in FIG. 2(B) is good.

The cosmetic use alternating current wave form WA2 is one in which when the electric potential level of the positive side and the electric potential level of the negative side are indicated with the reference electric potential as the mid-point, the alternating current wave form should consist of the indication of one of the levels of the two electric potential levels for the time of the 2nd reference time and the indication of the other of the electric potential levels for ½ of the time of the 2nd reference time as the 1st repetitive pattern W3 of the alternating current square-waves, and one of the levels of the two electric potential levels for ½ of the time of the 2nd reference time and the indication of the reference electric potential for ½ of the time of the 2nd reference time and the indication of the other of the electric potential levels for ½ of the time of the 2nd reference time as the 2nd repetitive pattern W4 of the alternating current square-waves, and the indication of the standard electric potential for ½ of the time of the 2nd reference time as pause P2, in the repetitive combination sequence of the first repetitive pattern W3, the pause P2, the first repetitive pattern W3, the pause P2, the 2nd repetitive pattern W4, the pause P2, the 2nd repetitive pattern W4 and the pause P2.

In the situation that is depicted in FIG. 2(B), for the above-described cosmetic use alternating current wave form WA2, the 2nd reference time has been set at 1.6 seconds. This means that the cosmetic use alternating current wave form WA2 that is depicted in FIG. 2(B) is that for which when the level of the electric potential on the positive side and the level of the electric potential on the negative side are indicated with the reference electric potential as the mid-point, the level of one of the afore-described two electric potential levels is indicated for 1.6 seconds, and the other electric potential is indicated for 0.8 seconds as the 1st repetitive pattern W3 of the alternating current square-waves, and the standard electric potential is indicated for 0.8 seconds and the level of the afore-described other electric potential level is indicated for 0.8 seconds as the 2nd repetitive pattern W4 of the alternating current square-waves, and the indication of the reference electric potential for 0.8 seconds forms the pause P2, in the repetitive combination sequence of the first repetitive pattern W3, the pause P2, the first repetitive pattern W3, the pause P2, the 2nd repetitive pattern W4, the pause P2, the 2nd repetitive pattern W4 and the pause P2.

The cycles of the cosmetic use alternating current wave form WA2 in which this series of alternating current square-wave patterns are combined is also composed in such a way that the cycle is 12.8 seconds as is the case with the above-described cosmetic use alternating current wave form WA1, and the wide area up-lift treatment should also be conducted repeatedly during the specified time with this cosmetic use alternating current wave form WA2.

After the wide area up-lift treatment described above has been completed, detailed areas of the face should be held down with one hand in a manner such as to lift-up that portion in order to conduct narrow area up-lift treatment in which detailed areas are lifted up. Such narrow area up-lift treatment was effective with the cosmetic use alternating current wave form WA3 that repetitively combines the alternating current square waves of different patterns that is depicted in FIG. 2(C).

For this cosmetic use alternating current wave form WA, the alternating current wave forms should be such that when the electric potential level of the positive side and the electric potential level of the negative side are indicated with the reference electric potential as the mid-point, one of the electric potential levels is indicated for the time of the 3rd reference time and the other level of the electric potential levels is indicated for the time of the 3rd reference time and one of the electric potential levels is indicated for the time of the 3rd reference time and the other level of the electric potential levels is indicated for the time of the 3rd reference time and the reference electric potential is indicated for twice the time of the 3rd reference time and one of the electric potential levels is indicated for ¼ of the time of the 3rd reference time and the reference electric potential is indicated for ½ of the time of the 3rd reference time and the other level of the electric potential levels is indicated for ¼ of the time of the 3rd reference time and the reference electric potential is indicated for the time of the 3rd reference time and the other level of the electric potential is indicated for ¼ of the time of the 3rd reference time and the reference electric potential is indicated for ½ of the time of the 3rd reference time and the other level of the electric potential levels is indicated for ¼ of the time of the 3rd reference time and the reference electric potential is indicated for the time of the 3rd reference time as the 3rd repetitive pattern W5 of the alternating current square-waves, and the reference electric potential is indicated for the time of the 3rd reference time and one of the electric potential levels is indicated for ¼ of the time of the 3rd reference time and the reference electric potential is indicated for ½ of the time of the 3rd reference time and one of the electric potential levels is indicated for ¼ of the time of the 3rd reference as the one directional repetitive pattern W6, and the reference electric potential is indicated for the time of the 3rd reference time and the other level of the electric potential levels is indicated for ¼ of the time of the 3rd reference time and the reference electric potential is indicated for ½ of the time of the 3rd reference time and the other level of the electric potential levels is indicated for ¼ of the time of the 3rd reference time as the other direction repetitive pattern W7, and the reference electric potential is indicated for the time of the 3rd reference time as pause P3 in the repetitive combination sequence of the 3rd repetitive pattern W5, the 3rd repetitive pattern W5, the one directional repetitive pattern W6, the other directional repetitive pattern W7, the pause P3, the one directional repetitive pattern W6, the other directional repetitive pattern W7, the pause P3 and the one directional repetitive pattern W6.

In the case of that which is depicted in FIG. 2(C), in the above-described cosmetic use alternating current wave forms, the situation is that for the above-described 3rd reference time, the same 0.4 second setting is used as with the afore-described 1st reference time which means that one of the levels of the afore-described two electric potential levels is output for 0.4 seconds and the afore-described other electric potential level is output for 0.4 seconds and one of the levels of the afore-described electrical potential levels is indicated for 0.4 seconds and the afore-described other electric potential level is output for 0.4 seconds and the afore-described reference electric potential is indicated for 0.8 seconds and one of the levels of the afore-described electric potential levels is output for 0.1 second and the above-described reference electric potential is output for 0.2 second and one of the levels of the afore-described electric potential levels is output for 0.1 second and the afore-described reference electric potential is indicated for 0.4 seconds and the afore-described other electric potential level is indicated for 0.1 second and the afore-described reference electric potential is indicated for 0.2 second and the afore-described other electric potential level is indicated for 0.1 second and the afore-described reference electric potential is indicated for 0.4 second as the 3rd repetitive pattern W5 of the alternating current square-waves, and the afore-described reference electric potential is indicated for 0.4 second and one of the levels of the afore-described electric potential levels is indicated for 0.1 second and the afore-described reference electric potential is indicated for 0.2 second and one of the levels of the afore-described electric potential levels is indicated for 0.1 second as the one directional repetitive pattern W6, and the afore-described reference electric potential is indicated for 0.4 second and the afore-described other electric potential level is indicated for 0.1 second and the afore-described reference electric potential is indicated for 0.2 second and the afore-described other electric potential level is indicated for 0.1 second as the other directional repetitive pattern W7, and the afore-described reference electric potential is indicated for 0.4 second as the pause P3 in a repetitive combination sequence of the 3rd repetitive pattern W5, the 3rd repetitive pattern W5, the one directional repetitive pattern W6, the other directional repetitive pattern W7, the pause P3, the one directional repetitive pattern W6, the other directional repetitive pattern W7, the pause P3, and the other directional repetitive pattern W7. The cosmetic use alternating current wave form WA3 too is repeated for its designated cycle of 12.8 seconds, and within the time allotted for the conducting electricity that is based on this cosmetic use alternating current wave form, the above-described narrow area treatment should be conducted.

In order to output the above-described three differing cosmetic use alternating current wave forms WA1, WA2 and WA3, after the cosmetic use alternating current wave form WA1 has been repeatedly output for the designated cycle time of 12.8 seconds from the electrical current control device 1, the design is such that there is an automatic output change by which the cosmetic use alternating current wave form WA2 is output. After that, there is the wave form output by which the cosmetic use alternating current wave form WA2 is repeatedly output for the designated cycle time of 12.8 seconds, and after that, there is an output change so that the cosmetic use alternating current wave form WA3 is automatically output. Then the cosmetic use alternating current wave form WA3 is repeatedly output for the designated cycle time of 12.8 seconds, and after this wave form output, the output is automatically stopped.

The changes in the above-described cosmetic use alternating current wave forms WA1, WA2 and WA3 should be used to repeat the preparatory treatment, the wide area treatment and the narrow area treatment, in which case, if the total is to take 15 minutes, then each of the 3 types of treatments can be conducted for 5 minutes each.

The output changes of the above-described combined cosmetic use alternating current wave forms WA1, WA2 and WA3 can be confirmed by means of the wave lamp 17 that is composed of three light emitting diodes (LEDs) that serve to correspond to each of the cosmetic use alternating current wave forms; by checking it [the wave lamp], it is possible to confirm which form is currently being output, thus making it possible to conduct the appropriate treatment.

In the explanation of the above description, as has been depicted in FIG. 2, the combination cosmetic use alternating wave forms WA1, WA2 and WA3 each have their electric potential set at ±0.3 V but it is permissible to change the voltage within eight levels that range from ±0.3 V to ±1.2 V. The range of the changes in voltage should be, for example, in the approximate range of 0.1 to 0.2 V.

In the explanation of the above description, treatment of the facial surface was conducted by means of selection of the facial select switch 11a, but if the body selection switch 11b is selected, parts of the body other than the face, that is to say, for example thus bust, the hips or such can be treated.

When the cosmetic use alternating current wave forms WA1, WA2 and WA3 described above as having been used on the face is used or a wave form combination thereof is used, it has been confirmed by experiments that the cosmetic effects obtained for the body have been the same as those obtained for the face. When using in such a manner on a body, the electric potential that is established should be such that in which when the range is, for example, ±0.9 V~±3.9 V, the change in electrical voltage can be actualized in eight stages. The voltage range of the change should, for example, be in the range of 0.4 to 0.6 V.

In Table 1 below is indicated the improvement effect on the wrinkles and sagging of the skin when stimulation by conducting electricity onto the face using the above-described cosmetic use alternating current wave form WA2 that is depicted in FIG. 2(B).

In Table 1 is depicted in the form of a comparison with the situation prior to applying the conduction of electrical stimulation; it indicates the situation when the conduction of electrical stimulation is applied using the cosmetic use alternating current wave form WA2. The evaluation of the wrinkles is based on the evaluation degrees indicated on Table 1, with the evaluation being conducted separately for the left side and the right side of the face of each of the subjects.

In Table 1, for example, with Subject 1, when skin treatment was conducted using the cosmetic use alternating wave form WA2, it is learned that there was no difference as compared to prior to the application. On the other hand, with Subject 2, the left side of the face, the wrinkles that were seen as being of a normal degree were alleviated to the extent that they were barely observed after treatment using the cosmetic use alternating current wave form WA2. On the right side of the face, it is learned that in contrast to the wrinkles that were initially evaluated as being between those of a normal degree and slight ones, they were, after the application, slight ones, thus indicating that there had been some alleviation of the wrinkles.

Such evaluations show that there is the same sort of improvement effect with the cosmetic use alternating wave forms WA1 and WA3. Furthermore, it is learned that even when such cosmetic use alternating wave forms WA1, WA2 and WA3 are used in serial combination, there is clearly a degree of improved effect that can be visually confirmed immediately after the treatment as compared to when one of the cosmetic use alternating wave forms WA1, WA2 and WA3 is used alone, with a longer length of time during which the improvement effect continues.

In the following Table 2 are depicted the results of having studied the improvement effects on sagging. The numerical values that appear in Table 2 reflect the time (in seconds) that it took the skin that had been pinched in a manner so as to fold the skin and then released to return to the state that it had been in prior to being pinched, and compares the resiliency of the skin. When skin has resiliency, the time that it takes for it to return to its former condition is short, and to that extent, it is unlikely for sagging to occur. Thus, it is possible to conduct an evaluation of the improvement effect on sagging by evaluating the resiliency of such skin.

TABLE 1

Effect of Improvements in Wrinkles

| Subject No. | Left External Canthus | | Right External Canthus | |
| --- | --- | --- | --- | --- |
| | Control | WA2 User | Control | WA2 User |
| 1 | 2.0 | 2.0 | 2.0 | 2.0 |
| 2 | 2.0 | 0.5 | 1.5 | 1.0 |
| 3 | 1.5 | 1.0 | 0.5 | 0.5 |
| 4 | 3.0 | 2.5 | 3.0 | 2.0 |
| 5 | 3.0 | 2.5 | 3.0 | 1.5 |
| Average | 2.3 | 1.7 | 2.0 | 1.4 |

*Evaluation Criteria
0: No wrinkles whatsoever seen.
1: Wrinkles barely seen.
2: Normal degree of wrinkles seen.
3: Wrinkles seen conspicuously.
4: Wrinkles seen dramatically.

TABLE 2

Effect of Improvements on Sagging

| Subject No. | Left External Canthus | | Right External Canthus | |
| --- | --- | --- | --- | --- |
| | Control | WA2 User | Control | WA2 User |
| 1 | 4.07 | 1.94 | 3.35 | 3.53 |
| 2 | 2.41 | 2.09 | 2.18 | 2.07 |
| 3 | 1.34 | 3.38 | 2.62 | 2.90 |
| 4 | 3.62 | 2.69 | 3.28 | 3.09 |
| 5 | 3.32 | 2.86 | 3.02 | 1.97 |
| Average | 2.95 | 2.69 | 2.88 | 2.71 |

*The numerical values indicated in the chart are those for the time (in seconds) that it takes for skin that has been pinched in manner such that the skin is folded over itself takes to return to its original condition when released. The lower this value is, the greater resilience the skin has and the less likely it is for such skin to sag.

From Table 2 it can be learned that by means of applying treatment to the face such that the cosmetic use alternating current wave forms in accordance with this invention are applied, there is, in all instances with the exception of the right side of the face of Subject 1 and of Subject 3, improvement to the resiliency of the skin as compared to what it was prior to the application. That means to say that even the "sagging" of skin that is based on deterioration in the resiliency of skin can be improved upon in the same manner by means of treatment that is performed in conjunction with passing electricity in a very weak current as stimulation with the alternating current wave form WA2 in accordance with this invention.

Figure 4:
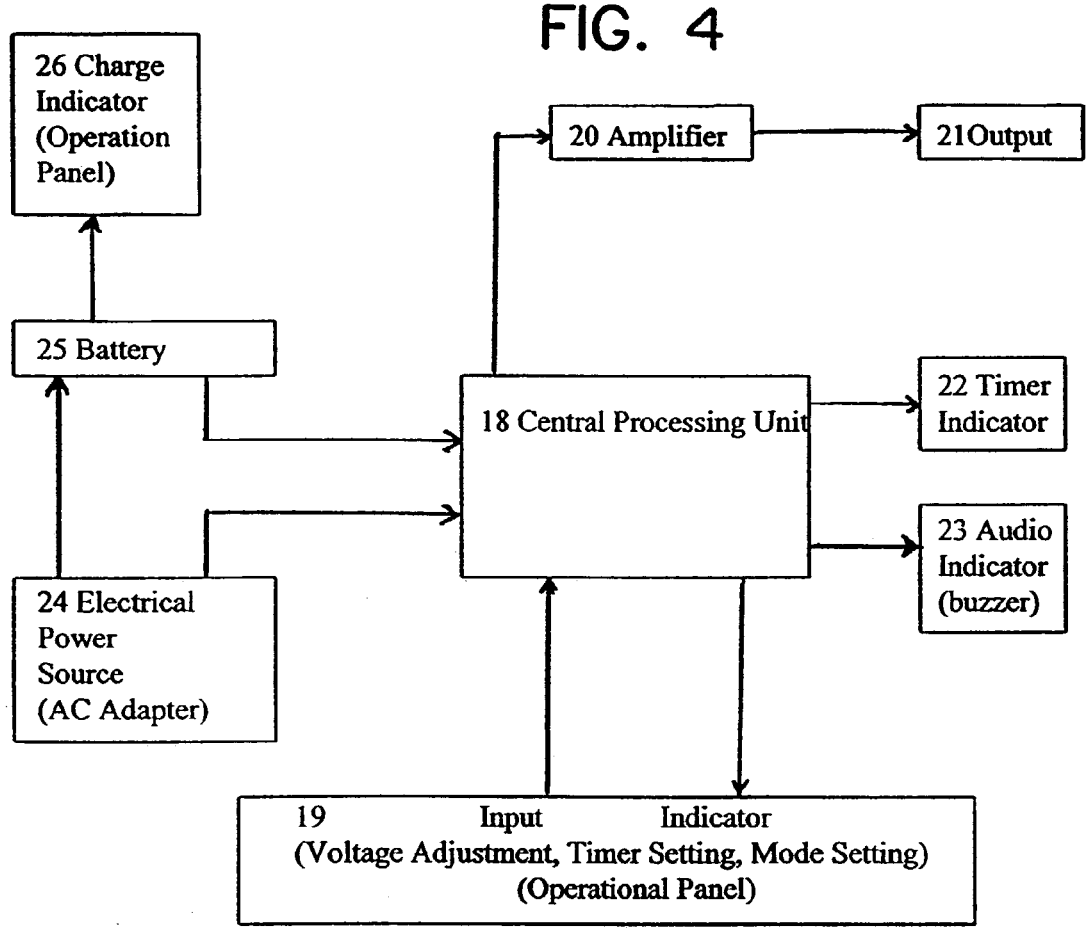
FIG. 4 is a block diagram depicting signal transmission routing within the electrical control device of the invention.

What happens is that the cosmetic use alternating current wave forms WA1, WA2 and WA3 of that which is explained in the above description are, as indicated in the block diagram of FIG. 4, output by operating the central processing unit (CPU) 18 that is built into the electrical current control device 1 by means of the input signal from the main switch 4a for turning ON the operation panel 19 that is connected to the central processing unit (CPU) 18 that is established within the electrical current control device 1, with the electrical current stimulation circuit being controlled by a program that has been down-loaded in advance into the central processing unit 18, through the amplifier 20 to the output side 21 that is composed of the output terminal 8. The cosmetic use alternating current wave forms WA1, WA2 and WA3 are supplied to the electrically conductive gloves 3a and 3b by connecting the electrically conductive gloves 3a and 3b to this output terminal 8.

Also, in terms of the operational circumstances due to the input signals from the operational panel 19, with the signals to the operational panel 19 from the central processing unit 18 it is possible to confirm, for example, the indications of the level at which the voltage has been set, the length of time that has been set, the model that has been set, and such. With the timer indicator 22, it is possible to indicate how much time remains. Furthermore, it is possible to form such that would draw the attention of the operator to the operational circumstances or mode changes by establishing the buzzer of audible indicator 23. Of course, it is also possible to recommend operational procedures by means of a synthesized voice.

The cosmetic use device in accordance with this invention is constructed so that it can be used with electrical power from a household use electrical power plug socket when the electrical power source 24 that makes up the alternating current adapter is connected to the central processing unit 18. In addition, the electrical power source 24 is such that it can be also connected to the battery 25 so that the charge indicator 26 confirms that it is connected to the battery 25 and indicates how much charge remains or that the charging has been completed. In cases wherein the cosmetic use device in accordance with this invention is to be used in a location where there is no electrical power plug socket, it is possible to use the device with a battery.

Figure 5:
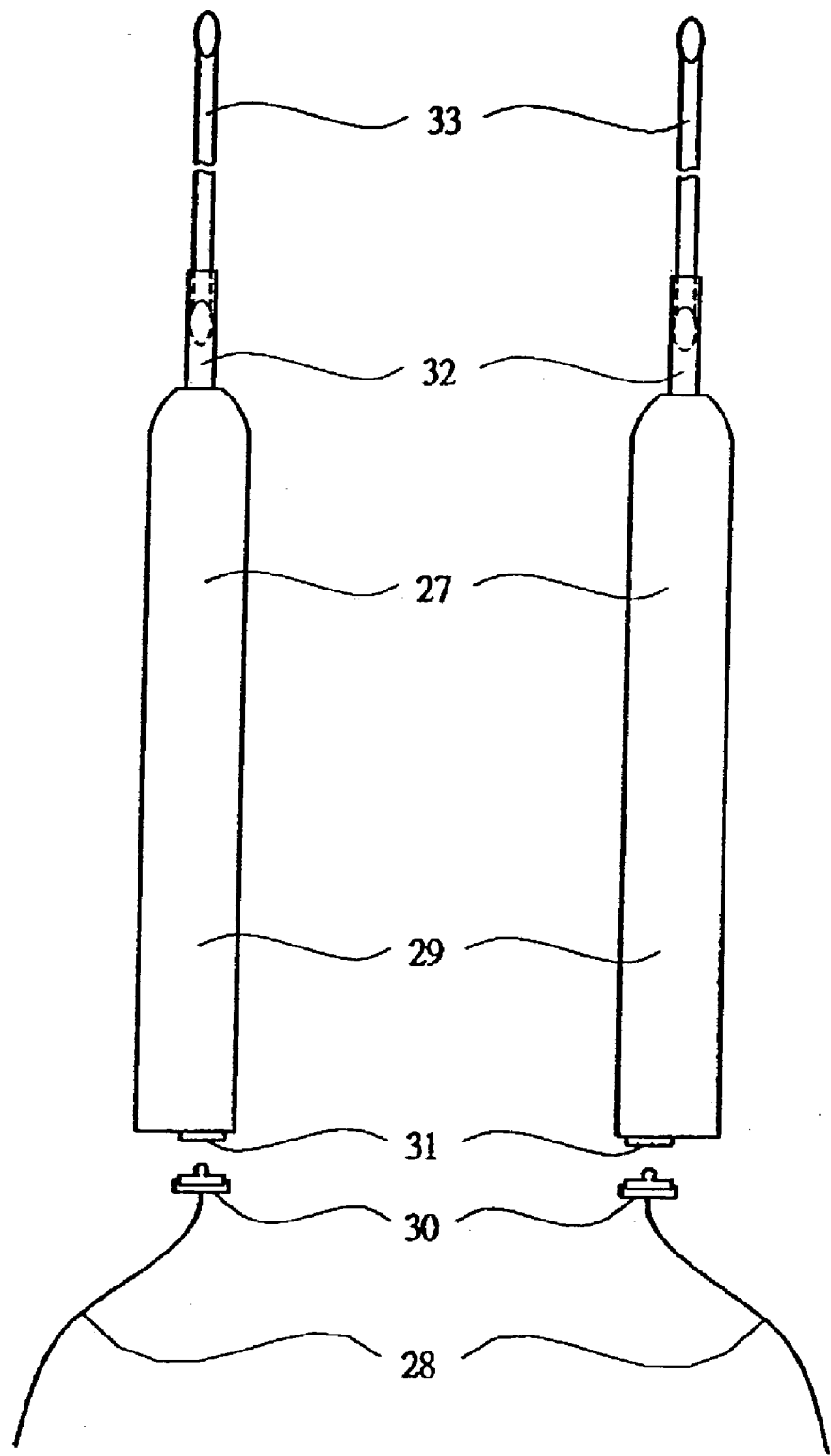
FIG. 5 is a frontal view depicting a pair of conductors used to conduct direct current.

Also, the above description is that which explains the construction by which the alternating current electricity is passed to the skin through the electrically conductive gloves 3a and 3b but with the electrical current control device 1, it is also possible to discharge a direct current through the connection cord 28 through the pair of conductors 27, as is indicated in FIG. 5 by establishing a direct current output terminal (not shown in the figures).

The pair of conductors 27 that are shown in FIG. 5 are composed of holder 29 that holds the conductor (not shown in the figures) for which the surroundings are surrounded by an insulation material through which passes the electricity that is connected to the connection cord 28. Hook 30 has been established for the connection cord 28 in a manner such as to permit attachment and removal at will with hook 31 that is on the other end of the conductor.

A cylindrical shaped holder 32 is established at the other end of the conductor, and, for example, it is possible to have inserted into this holder 32 on one end side something like cotton swabs 33 that has been wetted and can be disposed of easily when they becomes soiled.

Holder 32 should be such that a tubular shaped conductive material such as cotton swabs 33 can be inserted in advance somewhat snugly but in a manner such that removal and insertion can be performed at will. The switch (not shown in the figures) is turned ON when such as that of the composition of conductor 27 is connected to the electric current device 1 by means of connection cord 28. In this state, at the tips of the pair of cotton swabs 33 are brought into contact with the muscle portion in the manner that is depicted in FIG. 5 with the tips slightly apart. Direct current is conducted between the areas that the cotton swabs 24 are in contact with, and by means of the stimulation brought on by conducting the electricity, the tension of the muscle fibers and such is alleviated and a massage type of effect occurs.

Figure 6:
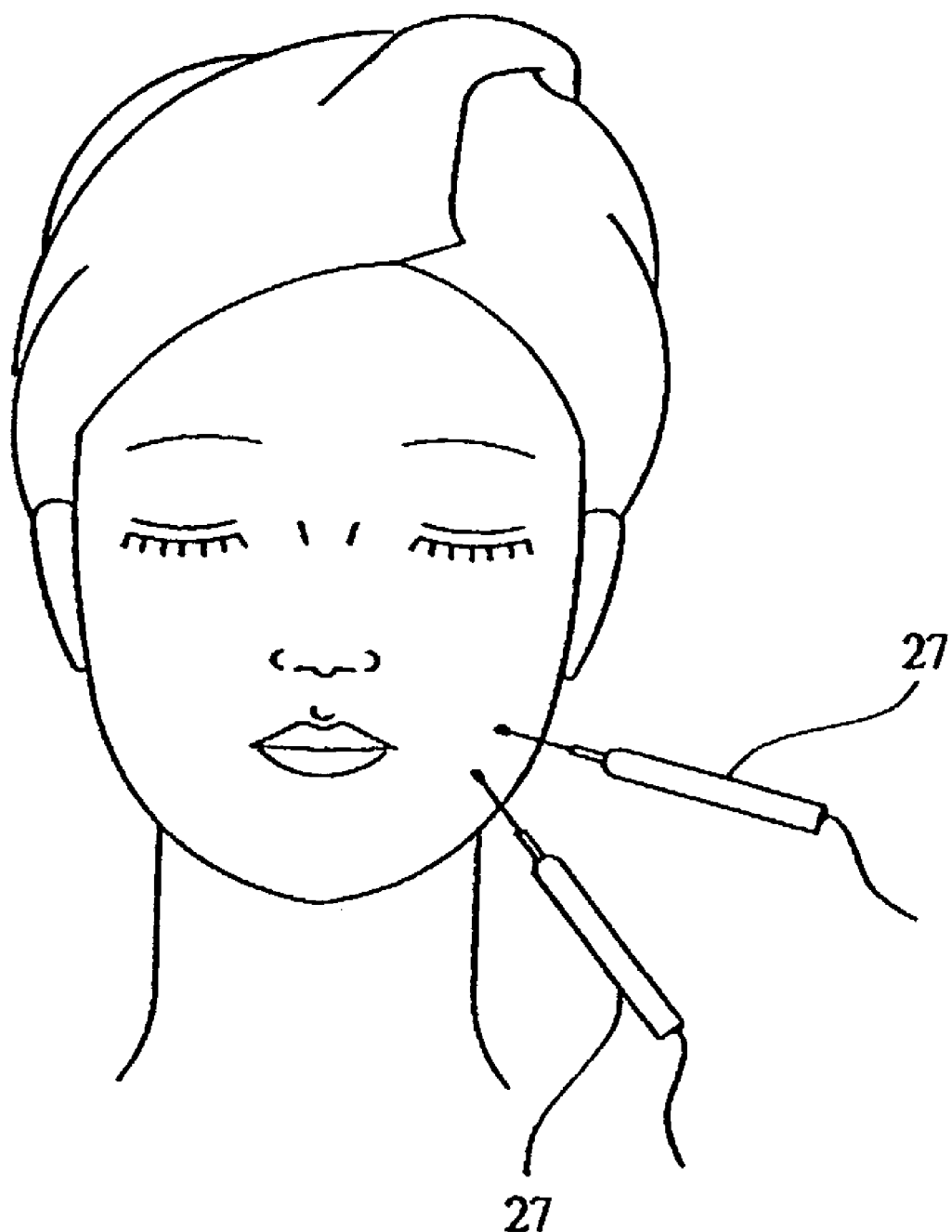
FIG. 6 is a frontal view depicting electricity being conducted to the muscle tissue portions of the face with the use of the conductors of FIG. 5.

If the above-described composition of the conductor 27 is a composition such that it can be used together with the electrical current control device 1, the composition of that which is indicated in FIG. 1, it is possible to selectively achieve from the same cosmetic use device the cosmetic effect that is indicated in FIG. 2 and the massage effect that is indicated in FIG. 6.

The composition should be such that the alternating currents and the direct currents of the electrical current control device 1 can be switched as required by means of a switch. As an alternative, an alternating current switch and a direct current switch could each be separately established.

This invention is not that which is limited only to the afore-described shape and form but rather, as long as it is within the scope of the fundamentals, it is that which can be changed in a variety of ways. In the above-described explanation, the cosmetic use device and the cosmetic use alternating current wave forms have been explained in the context of a situation wherein they are applied to the face but they can also be used for areas other than the face such as the bust, the hips, the scalp and the soles of the feet in order to obtain an up-lift type of effect, a massage effect or such. In the above-described explanation, electrically conductive gloves that include silver as a conductive material are used but it is possible to obtain the effects of the cosmetic use alternating current wave forms of this invention even if the conductive gloves that are used are those in which the conductive material is something other than silver.

The above-described explanation is one regarding a situation wherein the conductive material used for the conductive gloves is silver but it is possible to use a conductive material other than silver such as copper even if the conductivity of that material may be less. In the event that copper is used, for sensitive areas such as the face, the voltage should be ±0.5 V to ±5 V, and for areas such as the body, where the surface skin is relatively thick, the voltage should be ±0.5 V to ±10 V, with very weak electrical current that is 500 µA or less.

Also, in the above-described explanation, the person who puts on the electrically conductive gloves is described for a situation in which the objective is the cosmetic effect by the application of electrical stimulation through the electrically conductive gloves to that person's own face or such but of course applying electrical stimulation by bringing the conductive gloves into contact with the face or such of another person is an acceptable usage.

This invention is such that it is designed to alleviate wrinkles, sagging and such of the skin in the applied areas when it is applied to the face or parts of the body other than the face, thereby obtaining a cosmetic effect on the applied areas.

With this invention, because the electrically conductive gloves that include silver as a conductive material are being used, even if some other conductive material is used, it is possible to achieve good conductivity of with very weak electrical current, and it is possible to keep low the output electric potential in the cosmetic use device.

Also, in conjunction with the above-described composition, the composition is such that used together with a conductor through which direct electrical current is passed so as to obtain a massage effect on the muscle portion together with the cosmetic effect of an alleviation of the wrinkles, sagging and such of the skin, is possible.

By using a composition in which there is a holder in the conductor so that a conductive material such as cotton swabs that are common, inexpensive and disposable, it is possible to maintain a sanitary condition by periodically replacing that which is used as the conductor that would, under continued use, tend to become dirty, thereby making it possible to maintain the hygiene of the conductor. Because of this, even if the device is used by a plural number of people, hygiene can be easily maintained.

I claim:

1. A cosmetic device that comprises an electrical output device and a pair of electrical conductive gloves for electrical connection to said electrical output device, said pair of gloves containing an electrical conductive amount of an electrical conductive material such that the electrical conductive gloves have an electrical resistance of is 1 kΩ or less and whereby electrical current wave forms similar to the biological electrical currents that occur in the human body are adapted to be provided as cosmetic effects on skin of a patient by contacting the skin with the gloves that conduct electricity from the electrical output device through the gloves to the skin, wherein said electrical output device is adapted to repeatedly output an electrical voltage within the range of from about ±0.3V to about ±3.9V to said gloves as a combination of ultra-weak electrical currents that are comprised of a combination of multiple types of current wave forms made up of alternating current square-waves of differing patterns, such that when said gloves come into contact with the skin of the patient, said gloves pass through and apply to the skin a low electrical current of 500 μA or less in order to obtain skin beautification results.

2. A cosmetic device according to claim 1, wherein the said alternating current wave forms are provided with a 1st reference electric potential as a mid-point of an electric potential level on a positive side and the electric potential level on a negative side, repetitive alternating current wave form combinations are provided by repetitively combining the said alternating current wave forms provided as a single pattern in an alternating current square-wave pattern in a manner such that one level of the two electric potentials is provided and then, in turn, another electric potential is provided for the time of a 1st reference time, and a triple consecutive pattern in which the said single pattern is continued three times, and a pause for twice the time of the said 1st reference time in the sequence of the said triple consecutive pattern, the said pause, the said triple consecutive pattern, the said pause, the said single pattern, the said pause, the said single pattern, the said pause, the said single pattern, the said pause and the said single pattern, the said pause.

3. A cosmetic device according to claim 2, wherein the cosmetic device is a cosmetic device wherein the electrical current control device has an alternating output portion and a direct current output portion connected thereto and for connection to the pair of gloves as a pair of electrical conductors, and the cosmetic device provides a discharge electrical current that becomes electrical stimulation to skin when the pair of the said gloves comes into contact with skin of a patient.

4. A cosmetic device as claimed in claim 2, wherein said cosmetic device additionally comprises electrical conductors having holders that are electrically conductive, to which the electrically conductive gloves can be attached and detached at will, are held to discharge direct electrical current when the said conductive gloves come into contact with skin of a patient.

5. A cosmetic device as claimed in claim 2, wherein the electrical control device is adapted to repeatedly output the electrical voltage within the range of from about ±0.3V to about ±3.9V in a cycle time of about 12.8 seconds.

6. A cosmetic device as claimed in claim 2, wherein the electrical control device additionally comprises at least one voltage control switch for raising or lowering, within the voltage range of from about ±0.3V to about ±3.9V, the voltage output of the electrical control device.

7. A cosmetic device according to claim 1, wherein the said alternating current wave forms are provided with a reference electrical potential as a mid-point of the electrical potential level on the positive side and the electric potential level of the negative side, a repeated alternating current wave form combination is provided by a 1st repetitive alternating current wave form pattern providing one level of the two electric potential levels for the time of a 2nd reference time and providing the other level of the electric potential levels for ½ the time of the said 2nd reference time, and a 2nd repetitive alternating current wave form pattern providing the said one level of electric potential levels for ½ of the time of the said 2nd reference time, providing the aforementioned reference electric potential for ½ of the time of the said 2nd reference time and providing the said other level of electric potential for ½ of the time of the said reference time, and a pause providing the said electrical potential for ½ of the time of the said 2nd reference time in the sequence of the said 1St repetitive pattern, the said pause, the said 1st repetitive pattern, the said pause, the said 2nd repetitive pattern, the said pause, the said 2nd repetitive pattern and said pause.

8. A Cosmetic device according to claim 3, wherein the cosmetic device is a cosmetic device wherein the electrical current control device has an alternating output portion and a direct current output portion connected thereto and for connection to the pair of gloves as a pair of electrical conductors, and the cosmetic device provides a discharge electrical current that becomes electrical stimulation to skin when the pair of the said gloves comes into contact with skin of a patient.

9. A cosmetic device as claimed in claim 7, wherein said cosmetic device additionally comprises electrical conductors having holders that are electrically conductive, to which the electrically conductive gloves can be attached and detached at will, are held to discharge direct electrical current when the said conductive gloves come into contact with skin of a patient.

10. A cosmetic device as claimed in claim 7, wherein the electrical control device is adapted to repeatedly output the electrical voltage within the range of from about ±0.3V to about ±3.9V in a cycle time of about 12.8 seconds.

11. A cosmetic device as claimed in claim 7, wherein the electrical control device additionally comprises at least one voltage control switch for raising or lowering, within the voltage range of from about ±0.3V to about ±3.9V, the voltage output of the electrical control device.

12. A cosmetic device according to claim 1, wherein the said alternating current wave forms are provided with a 1st reference electric potential as a mid-point of the electric potential level on the positive side and the electric potential level on the negative side, the repeated alternating current wave form combination are provided by a 3rd repetitive alternating current wave form pattern providing one of two electrical potential levels for the time of a 3rd reference time and providing the afore-mentioned other level of the electric potential levels for the time of the said 3rd reference time and providing the other level of the electric potential levels for the time of the said 3rd reference time and providing the said reference electric potential for twice the time of the said 3rd reference time and providing the said other level of the electric potential levels for ¼ of the time of the said 3rd reference time and providing the said reference electric potential for ½ of the time of the said 3rd reference time and providing the said other level of electric potential levels for ¼ of the time of the said 3rd reference time and providing the said reference electric potential for the time of the said 3rd reference time and providing the said other level of the electric potential levels for ¼ of the time of the said 3rd reference time and providing the reference electric potential for ½ of the time of the 3rd reference time and providing the said other level of the electric potential levels for ¼ of the time of the 3rd reference time and providing the said reference electric potential for the time of the said reference time, and a repetitive pattern in one direction providing the said reference electric potential for the time of the said 3rd reference time and providing the said one electric potential level for the ¼ of time of the said 3rd reference time and providing the said reference electric potential for the ½ of time of the said 3rd reference time and providing the said one level of the electric potential levels for the ¼ time of the said 3rd reference time, and a repetitive pattern in the other direction providing the said reference electric potential for the time of the said 3rd reference time and providing the said other level of the electric potential levels for the ¼ of the time of the said 3rd reference time and providing the said reference electric potential for the ½ of the time of the said 3rd reference time and providing the said other level of the electric potential levels for the ¼ of the time of the said 3rd reference time, and a pause providing the said electrical potential for the time of the said 3rd reference time in the sequence of the said 3rd repetitive pattern, the said 3rd repetitive pattern, the said repetitive pattern in one direction, the said repetitive pattern in the other direction, the said pause, the said repetitive pattern in one direction, the said repetitive pattern in the other direction, the said pause, and the said repetitive pattern in one direction.

13. A cosmetic device according to claim 12, wherein the cosmetic device is a cosmetic device wherein the electrical current control device has an alternating output portion and a direct current output portion connected thereto and for connection to the pair of gloves as a pair of electrical conductors, and the cosmetic device provides a discharge electrical current that becomes electrical stimulation to skin when the pair of the said gloves comes into contact with skin of a patient.

14. A cosmetic device as claimed in claim 12, wherein said cosmetic device additionally comprises electrical conductors having holders that are electrically conductive, to which the electrically conductive gloves can be attached and detached at will, are held to discharge direct electrical current when the said conductive gloves come into contact with skin of a patient.

15. A cosmetic device as claimed in claim 12, wherein the electrical control device is adapted to repeatedly output the electrical voltage within the range of from about ±0.3V to about ±3.9V in a cycle time of about 12.8 seconds.

16. A cosmetic device as claimed in claim 12, wherein the electrical control device additionally comprises at least one voltage control switch for raising or lowering, within the voltage range of from about ±0.3V to about ±3.9V, the voltage output of the electrical control device.

17. A cosmetic device according to claim 1, wherein the alternating current wave form is such that it is characterized by the alternating current wave form described in claim 2 is provided, then the alternating current wave form described in claim 3 is provided, and then the alternating current wave form described in claim 4 is provided, with the said 2nd reference time established as quadruple the time of the said 1st reference time and the said 3rd reference time established to be equal to the time of the said 1st reference time.

18. A cosmetic device according to claim 17, wherein the said 1st reference time is 0.4 second.

19. A cosmetic device according to claim 17, wherein the cosmetic device is a cosmetic device wherein the electrical current control device has an alternating output portion and a direct current output portion connected thereto and for connection to the pair of gloves as a pair of electrical conductors, and the cosmetic device provides a discharge electrical current that becomes electrical stimulation to skin when the pair of the said gloves comes into contact with skin of a patient.

20. A cosmetic device as claimed in claim 17, wherein said cosmetic device additionally comprises electrical conductors having holders that are electrically conductive, to which the electrically conductive gloves can be attached and detached at will, are held to discharge direct electrical current when the said conductive gloves come into contact with skin of a patient.

21. A cosmetic device according to claim 1, wherein the cosmetic device is a cosmetic device wherein the electrical current control device has an alternating output portion and a direct current output portion connected thereto and for connection to the pair of gloves as a pair of electrical conductors, and the cosmetic device provides a discharge electrical current that becomes electrical stimulation to skin when the pair of the said gloves comes into contact with skin of a patient.

22. A cosmetic device as claimed in claim 1, wherein said cosmetic device additionally comprises electrical conductors having holders that are electrically conductive, to which the electrically conductive gloves can be attached and detached at will, are held to discharge direct electrical current when the said conductive gloves come into contact with skin of a patient.

23. A cosmetic device as claimed in claim 1, wherein the electrical control device is adapted to repeatedly output the electrical voltage within the range of from about ±0.3V to about ±3.9V in a cycle time of about 12.8 seconds.

24. A cosmetic device as claimed in claim 1, wherein the electrical control device additionally comprises at least one voltage control switch for raising or lowering, within the voltage range of from about ±0.3V to about ±3.9V, the voltage output of the electrical control device.

* * * * *